United States Patent
Kostrzewski

(10) Patent No.: US 11,806,100 B2
(45) Date of Patent: *Nov. 7, 2023

(54) ROBOTIC SURGICAL SYSTEMS

(71) Applicant: KB MEDICAL, SA, Audubon, PA (US)

(72) Inventor: Szymon Kostrzewski, Lausanne (CH)

( * ) Notice: Subject to any disclaimer, the term of this patent is extended or adjusted under 35 U.S.C. 154(b) by 22 days.

This patent is subject to a terminal disclaimer.

(21) Appl. No.: 17/352,505

(22) Filed: Jun. 21, 2021

(65) Prior Publication Data
US 2021/0307848 A1 Oct. 7, 2021

Related U.S. Application Data

(63) Continuation of application No. 15/790,538, filed on Oct. 23, 2017, now Pat. No. 11,039,893.

(60) Provisional application No. 62/411,258, filed on Oct. 21, 2016.

(51) Int. Cl.
| | |
|---|---|
| *G05B 15/00* | (2006.01) |
| *G05B 19/00* | (2006.01) |
| *A61B 34/30* | (2016.01) |
| *A61B 34/10* | (2016.01) |
| *B25J 9/16* | (2006.01) |
| *B25J 15/00* | (2006.01) |
| *A61B 34/00* | (2016.01) |
| *A61B 90/11* | (2016.01) |
| *A61B 34/20* | (2016.01) |

(52) U.S. Cl.
CPC .............. *A61B 34/30* (2016.02); *A61B 34/10* (2016.02); *A61B 34/76* (2016.02); *A61B 90/11* (2016.02); *B25J 9/1633* (2013.01); *B25J 9/1679* (2013.01); *B25J 15/0019* (2013.01); *A61B 2034/107* (2016.02); *A61B 2034/2051* (2016.02); *A61B 2034/2055* (2016.02); *A61B 2034/304* (2016.02); *B25J 9/1602* (2013.01); *Y10S 901/09* (2013.01)

(58) Field of Classification Search
CPC ......... A61B 34/30; A61B 34/10; A61B 34/76; A61B 90/11; A61B 2034/107; A61B 2034/2051; A61B 2034/2055; A61B 2034/304; B25J 9/1633; B25J 9/1679; B25J 15/0019; B25J 9/1602; Y10S 901/09
See application file for complete search history.

(56) References Cited

U.S. PATENT DOCUMENTS

| | | |
|---|---|---|
| 4,150,293 A | 4/1979 | Franke |
| 5,246,010 A | 9/1993 | Gazzara et al. |
| 5,598,453 A | 1/1997 | Baba et al. |

(Continued)

*Primary Examiner* — Harry Y Oh
*Assistant Examiner* — Sohana Tanju Khayer
(74) *Attorney, Agent, or Firm* — Vamsi Kakarla

(57) ABSTRACT

A robotic surgical system for performing surgery, the system includes a robotic arm having a force and/or torque control sensor coupled to the end-effector and configured to hold a first surgical tool. The robotic system further includes an actuator that includes controlled movement of the robotic arm and/or positioning of the end-effector. The system further includes a tracking detector having optical markers for real time detection of (i) surgical tool position and/or end-effector position and (ii) patient position. The system also includes a feedback system for moving the end effector to a planned trajectory based on the threshold distance between the planned trajectory and the actual trajectory.

17 Claims, 14 Drawing Sheets

(56) References Cited

U.S. PATENT DOCUMENTS

| | | |
|---|---|---|
| 5,772,594 A | 6/1998 | Barrick |
| 5,987,960 A | 11/1999 | Messner et al. |
| 6,031,888 A | 2/2000 | Ivan et al. |
| 6,144,875 A | 11/2000 | Schweikard et al. |
| 6,203,196 B1 | 3/2001 | Meyer et al. |
| 6,306,126 B1 | 10/2001 | Montezuma |
| 6,314,311 B1 | 11/2001 | Williams et al. |
| 6,320,929 B1 | 11/2001 | Von Der Haar |
| 6,477,400 B1 | 11/2002 | Barrick |
| 6,484,049 B1 | 11/2002 | Seeley et al. |
| 6,487,267 B1 | 11/2002 | Wolter |
| 6,490,475 B1 | 12/2002 | Seeley et al. |
| 6,501,981 B1 | 12/2002 | Schweikard et al. |
| 6,535,756 B1 | 3/2003 | Simon et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,666,579 B2 | 12/2003 | Jensen |
| 6,757,068 B2 | 6/2004 | Foxlin |
| 6,782,287 B2 | 8/2004 | Grzeszczuk et al. |
| 6,856,826 B2 | 2/2005 | Seeley et al. |
| 6,856,827 B2 | 2/2005 | Seeley et al. |
| 6,920,347 B2 | 7/2005 | Simon et al. |
| 6,922,632 B2 | 7/2005 | Foxlin |
| 6,988,009 B2 | 1/2006 | Grimm et al. |
| 6,996,487 B2 | 2/2006 | Jutras et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,301,648 B2 | 11/2007 | Foxlin |
| 7,313,430 B2 | 12/2007 | Urquhart et al. |
| 7,318,805 B2 | 1/2008 | Schweikard et al. |
| 7,324,623 B2 | 1/2008 | Heuscher et al. |
| 7,327,865 B2 | 2/2008 | Fu et al. |
| 7,460,637 B2 | 12/2008 | Clinthorne et al. |
| 7,493,153 B2 | 2/2009 | Ahmed et al. |
| 7,505,617 B2 | 3/2009 | Fu et al. |
| 7,623,902 B2 | 11/2009 | Pacheco |
| 7,643,862 B2 * | 1/2010 | Schoenefeld .......... A61B 90/36 600/407 |
| 7,661,881 B2 | 2/2010 | Gregerson et al. |
| 7,683,331 B2 | 3/2010 | Chang |
| 7,683,332 B2 | 3/2010 | Chang |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,725,253 B2 | 5/2010 | Foxlin |
| 7,726,171 B2 | 6/2010 | Langlotz et al. |
| 7,760,849 B2 | 7/2010 | Zhang |
| 7,796,728 B2 | 9/2010 | Bergfjord |
| 7,813,838 B2 | 10/2010 | Sommer |
| 7,835,778 B2 | 11/2010 | Foley et al. |
| 7,835,784 B2 | 11/2010 | Mire et al. |
| 7,840,256 B2 | 11/2010 | Lakin et al. |
| 7,844,320 B2 | 11/2010 | Shahidi |
| 7,853,305 B2 | 12/2010 | Simon et al. |
| 7,853,313 B2 | 12/2010 | Thompson |
| 7,900,524 B2 | 3/2011 | Calloway et al. |
| 7,940,999 B2 | 5/2011 | Liao et al. |
| 7,945,012 B2 | 5/2011 | Ye et al. |
| 7,945,021 B2 | 5/2011 | Shapiro et al. |
| 8,019,045 B2 | 9/2011 | Kato |
| 8,021,310 B2 | 9/2011 | Sanborn et al. |
| 8,052,688 B2 | 11/2011 | Wolf, II |
| 8,086,299 B2 | 12/2011 | Adler et al. |
| 8,098,914 B2 | 1/2012 | Liao et al. |
| 8,100,950 B2 | 1/2012 | St. Clair et al. |
| 8,116,430 B1 | 2/2012 | Shapiro et al. |
| 8,121,249 B2 | 2/2012 | Wang et al. |
| 8,150,494 B2 | 4/2012 | Simon et al. |
| 8,208,708 B2 | 6/2012 | Homan et al. |
| 8,224,024 B2 | 7/2012 | Foxlin et al. |
| 8,311,611 B2 | 11/2012 | Csavoy et al. |
| 8,335,557 B2 | 12/2012 | Maschke |
| 8,358,818 B2 | 1/2013 | Miga et al. |
| 8,379,791 B2 | 2/2013 | Forthmann et al. |
| 8,386,019 B2 | 2/2013 | Camus et al. |
| 8,394,099 B2 | 3/2013 | Patwardhan |
| 8,462,911 B2 | 6/2013 | Vesel et al. |
| 8,526,700 B2 | 9/2013 | Isaacs |
| 8,541,970 B2 | 9/2013 | Nowlin et al. |
| 8,560,118 B2 | 10/2013 | Greer et al. |
| 8,597,198 B2 | 12/2013 | Sanborn et al. |
| 8,611,985 B2 | 12/2013 | Lavallee et al. |
| 8,630,389 B2 | 1/2014 | Kato |
| 8,634,897 B2 | 1/2014 | Simon et al. |
| 8,660,635 B2 | 2/2014 | Simon et al. |
| 8,678,647 B2 | 3/2014 | Gregerson et al. |
| 8,696,458 B2 | 4/2014 | Foxlin et al. |
| 8,706,185 B2 | 4/2014 | Foley et al. |
| 8,727,618 B2 | 5/2014 | Maschke et al. |
| 8,738,115 B2 | 5/2014 | Amberg et al. |
| 8,740,882 B2 | 6/2014 | Jun et al. |
| 8,781,186 B2 | 7/2014 | Clements et al. |
| 8,781,630 B2 | 7/2014 | Banks et al. |
| 8,787,520 B2 | 7/2014 | Baba |
| 8,792,704 B2 | 7/2014 | Isaacs |
| 8,798,231 B2 | 8/2014 | Notohara et al. |
| 8,812,077 B2 | 8/2014 | Dempsey |
| 8,814,793 B2 | 8/2014 | Brabrand |
| 8,818,105 B2 | 8/2014 | Myronenko et al. |
| 8,821,511 B2 | 9/2014 | Von Jako et al. |
| 8,867,703 B2 | 10/2014 | Shapiro et al. |
| 8,888,821 B2 | 11/2014 | Rezach et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,561,082 B2 * | 2/2017 | Yen ....................... A61B 34/30 |
| 9,592,096 B2 | 3/2017 | Maillet et al. |
| 9,675,272 B2 * | 6/2017 | Selover ................. A61B 5/742 |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2004/0016077 A1 * | 1/2004 | Song ...................... A47L 9/009 15/340.1 |
| 2004/0076259 A1 | 4/2004 | Jensen et al. |
| 2006/0184396 A1 | 8/2006 | Dennis et al. |
| 2006/0247517 A1 * | 11/2006 | Labadie ................ A61B 90/36 600/426 |
| 2006/0291612 A1 | 12/2006 | Nishide et al. |
| 2007/0038059 A1 | 2/2007 | Sheffer et al. |

(56) References Cited

U.S. PATENT DOCUMENTS

| | | |
|---|---|---|
| 2007/0073133 A1 | 3/2007 | Schoenefeld |
| 2008/0004523 A1 | 1/2008 | Jensen |
| 2008/0013809 A1 | 1/2008 | Zhu et al. |
| 2008/0082109 A1 | 4/2008 | Moll et al. |
| 2008/0108991 A1 | 5/2008 | von Jako |
| 2008/0144906 A1 | 6/2008 | Allred et al. |
| 2008/0161680 A1 | 7/2008 | von Jako et al. |
| 2008/0235052 A1 | 9/2008 | Node-Langlois et al. |
| 2008/0269596 A1 | 10/2008 | Revie et al. |
| 2008/0287781 A1 | 11/2008 | Revie et al. |
| 2008/0300477 A1 | 12/2008 | Lloyd et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0185655 A1 | 7/2009 | Koken et al. |
| 2009/0198121 A1 | 8/2009 | Hoheisel |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0228117 A1 | 9/2010 | Hartmann |
| 2010/0274120 A1 | 10/2010 | Heuscher |
| 2011/0098553 A1 | 4/2011 | Robbins et al. |
| 2011/0282189 A1 | 11/2011 | Graumann |
| 2011/0286573 A1 | 11/2011 | Schretter et al. |
| 2012/0035507 A1 | 2/2012 | George et al. |
| 2012/0051498 A1 | 3/2012 | Koishi |
| 2012/0143084 A1 | 6/2012 | Shoham |
| 2012/0226145 A1 | 9/2012 | Chang et al. |
| 2012/0235909 A1 | 9/2012 | Birkenbach et al. |
| 2012/0294498 A1 | 11/2012 | Popovic |
| 2013/0016889 A1 | 1/2013 | Myronenko et al. |
| 2013/0060146 A1 | 3/2013 | Yang et al. |
| 2013/0094742 A1 | 4/2013 | Feilkas |
| 2013/0113791 A1 | 5/2013 | Isaacs et al. |
| 2013/0165937 A1 | 6/2013 | Patwardhan |
| 2013/0281821 A1 | 10/2013 | Liu et al. |
| 2013/0307955 A1 | 11/2013 | Deitz et al. |
| 2013/0342578 A1 | 12/2013 | Isaacs |
| 2013/0345757 A1 | 12/2013 | Stad |
| 2014/0046132 A1 | 2/2014 | Hoeg et al. |
| 2014/0049629 A1 | 2/2014 | Siewerdsen et al. |
| 2014/0080086 A1 | 3/2014 | Chen |
| 2014/0096369 A1 | 4/2014 | Matsumoto et al. |
| 2014/0121676 A1 | 5/2014 | Kostrzewski et al. |
| 2014/0135796 A1 | 5/2014 | Simon et al. |
| 2014/0130810 A1 | 8/2014 | Azizian et al. |
| 2014/0221819 A1 | 8/2014 | Sarment |
| 2014/0234804 A1 | 8/2014 | Huang et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0100066 A1* | 4/2015 | Kostrzewski .......... A61B 90/06 606/130 |
| 2015/0146847 A1 | 5/2015 | Liu |
| 2015/0150524 A1 | 6/2015 | Yorkston et al. |
| 2015/0182285 A1* | 7/2015 | Yen .................. A61B 17/1626 606/86 R |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0035404 A1* | 2/2017 | Foster .................... A61B 1/32 |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0165837 A1* | 6/2017 | Asano .................. B25J 9/1674 |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

* cited by examiner

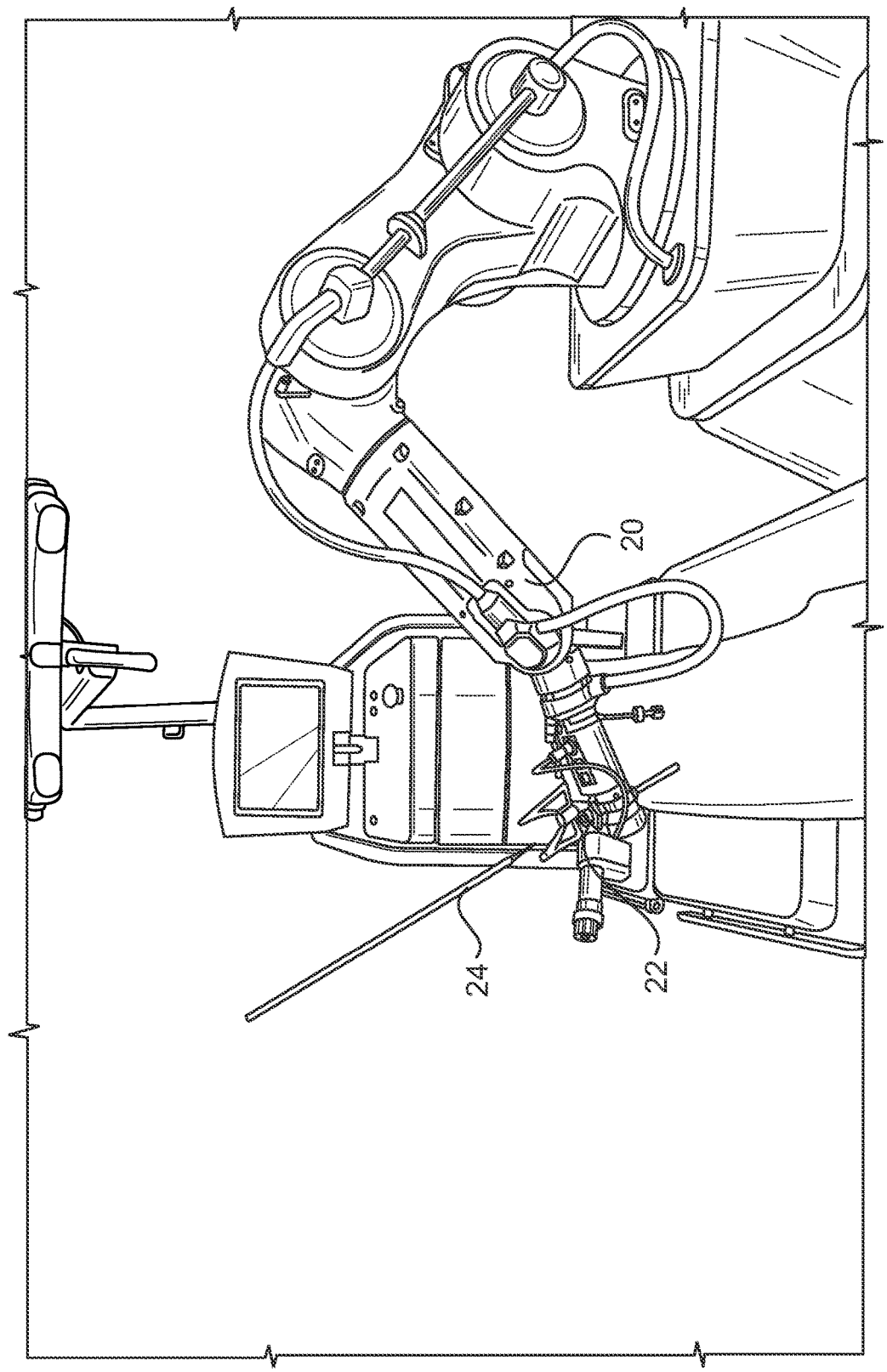

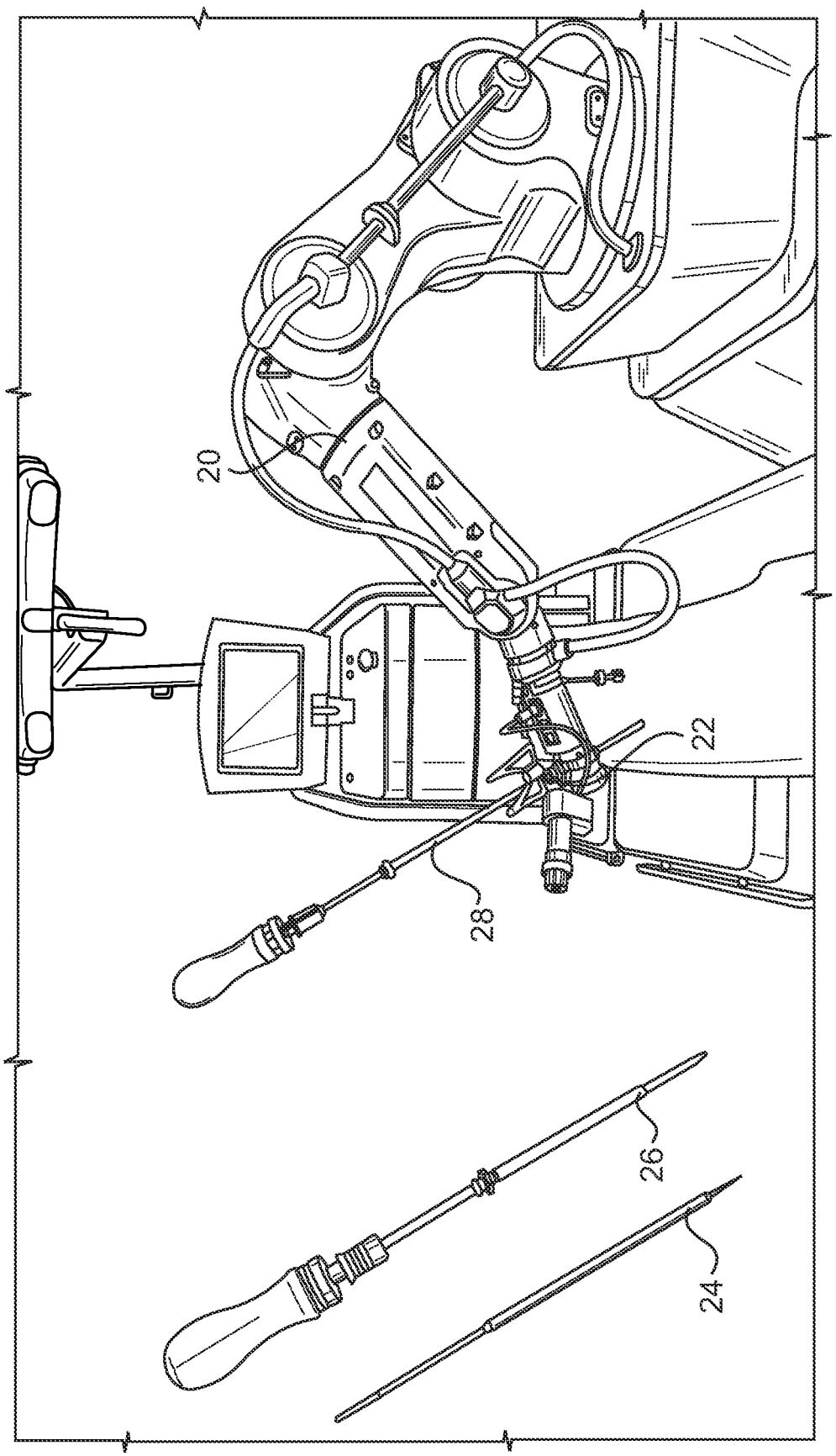

PLAN TRAJECTORY

PUNCH CORTICAL BONE WITH AN AWL (OPTONAL)

ROBOT TRAJECTORY-LOCK MODE FOLLOWS ADVANCEMENT OF AN INSTRUMENT

SREW PLACEMENT IN THE PREPARED HOLE

ROBOTIC SURGICAL SYSTEMS

CROSS-REFERENCE TO RELATED APPLICATIONS

This application is a continuation of U.S. application Ser. No. 15/790,538, filed on Oct. 23, 2017, which claims priority to U.S. provisional application Ser. No. 62/411,258, filed on Oct. 21, 2016, all of which are incorporated herein by reference.

BACKGROUND

Robotic-assisted surgical systems have been developed to improve surgical precision and enable the implementation of new surgical procedures. For example, robotic systems have been developed to sense a surgeon's hand movements and translate them to scaled-down micro-movements and filter out unintentional tremors for precise microsurgical techniques in organ transplants, reconstructions, and minimally invasive surgeries. Feedback-controlled robotic systems have also been developed to provide smoother manipulation of a surgical tool during a procedure than could be achieved by an unaided surgeon.

However, widespread acceptance of robotic systems by surgeons and hospitals is limited for a variety of reasons. Current systems are expensive to own and maintain. They often require extensive preoperative surgical planning prior to use, and they extend the required preparation time in the operating room. They are physically intrusive, possibly obscuring portions of a surgeon's field of view and blocking certain areas around the operating table, such that a surgeon and/or surgical assistants are relegated to one side of the operating table. Current systems may also be non-intuitive or otherwise cumbersome to use, particularly for surgeons who have developed a special skill or "feel" for performing certain maneuvers during surgery and who find that such skill cannot be implemented using the robotic system. Finally, robotic surgical systems may be vulnerable to malfunction or operator error, despite safety interlocks and power backups.

Spinal surgeries often require precision drilling and placement of screws or other implements in relation to the spine, and there may be constrained access to the vertebrae during surgery that makes such maneuvers difficult. Catastrophic damage or death may result from improper drilling or maneuvering of the body during spinal surgery, due to the proximity of the spinal cord and arteries. Common spinal surgical procedures include a discectomy for removal of all or part of a disk, a foraminotomy for widening of the opening where nerve roots leave the spinal column, a laminectomy for removal of the lamina or bone spurs in the back, and spinal fusion for fusing of two vertebrae or vertebral segments together to eliminate pain caused by movement of the vertebrae.

Spinal surgeries that involve screw placement require preparation of holes in bone (e.g., vertebral segments) prior to placement of the screws. Where such procedures are performed manually, in some implementations, a surgeon judges a drill trajectory for subsequent screw placement on the basis of pre-operative CT scans. Other manual methods which do not involve usage of the pre-operative CT scans, such as fluoroscopy, 3D fluoroscopy or natural landmark-based, may be used to determine the trajectory for preparing holes in bone prior to placement of the screws. In some implementations, the surgeon holds the drill in his hand while drilling, and fluoroscopic images are obtained to verify if the trajectory is correct. Some surgical techniques involve usage of different tools, such as a pedicle finder or K-wires. Such procedures rely strongly on the expertise of the surgeon, and there is significant variation in success rate among different surgeons. Screw misplacement is a common problem in such surgical procedures.

Image-guided spinal surgeries involve optical tracking to aid in screw placement. However, such procedures are currently performed manually, and surgical tools can be inaccurately positioned despite virtual tracking. A surgeon is required to coordinate his real-world, manual manipulation of surgical tools using images displayed on a two dimensional screen. Such procedures can be non-intuitive and require training, since the surgeon's eye must constantly scan both the surgical site and the screen to confirm alignment. Furthermore, procedural error can result in registration inaccuracy of the image-guiding system, rendering it useless, or even misleading. Thus, there is a need for a system for stabilizing surgical instruments while allowing the instruments and the instrument holder to be both easily sterilized and installed and removed from the robotic system without deteriorating localization precision as well as attachment rigidity.

SUMMARY OF THE INVENTION

In an exemplary embodiment, a robotic surgical system includes a robotic arm comprising a force and/or torque control end-effector configured to hold a first surgical tool; an actuator for controlled movement of the robotic arm and/or positioning of the end-effector; a tracking detector for real time detection of surgical tool position and/or end-effector position and patient position; and a processor and a non-transitory computer readable medium storing instructions thereon wherein the instructions, when executed, cause the processor to: access or generate a virtual representation of a patient situation; obtain a real-time surgical tool position and/or end-effector position and patient position from the tracking detector; and maintain a surgical instrument along a pre-planned trajectory that is stored in the non-transitory computer readable medium.

In another exemplary embodiment, the instructions, when executed, cause the processor to: determine the instrument is within a threshold distance of the pre-planned trajectory; and move the robotic arm such that the instrument is appropriately aligned with the trajectory.

In another exemplary embodiment, the threshold distance is greater than zero (e.g., greater than 0.1 cm, 0.5 cm, or 1 cm) and less than 1 meter (e.g., less than 20 cm, 10 cm, 5 cm, 3 cm).

In other embodiments, the surgical robotic system may be used with pre-programmed/pre-planned trajectories and/or surgeries. In one exemplary embodiment, the robotic surgical system can move automatically based on sensor data and artificial intelligence.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIGS. 3A-3C illustrate a universal instrument guide and associated method of use;

Figure 1:
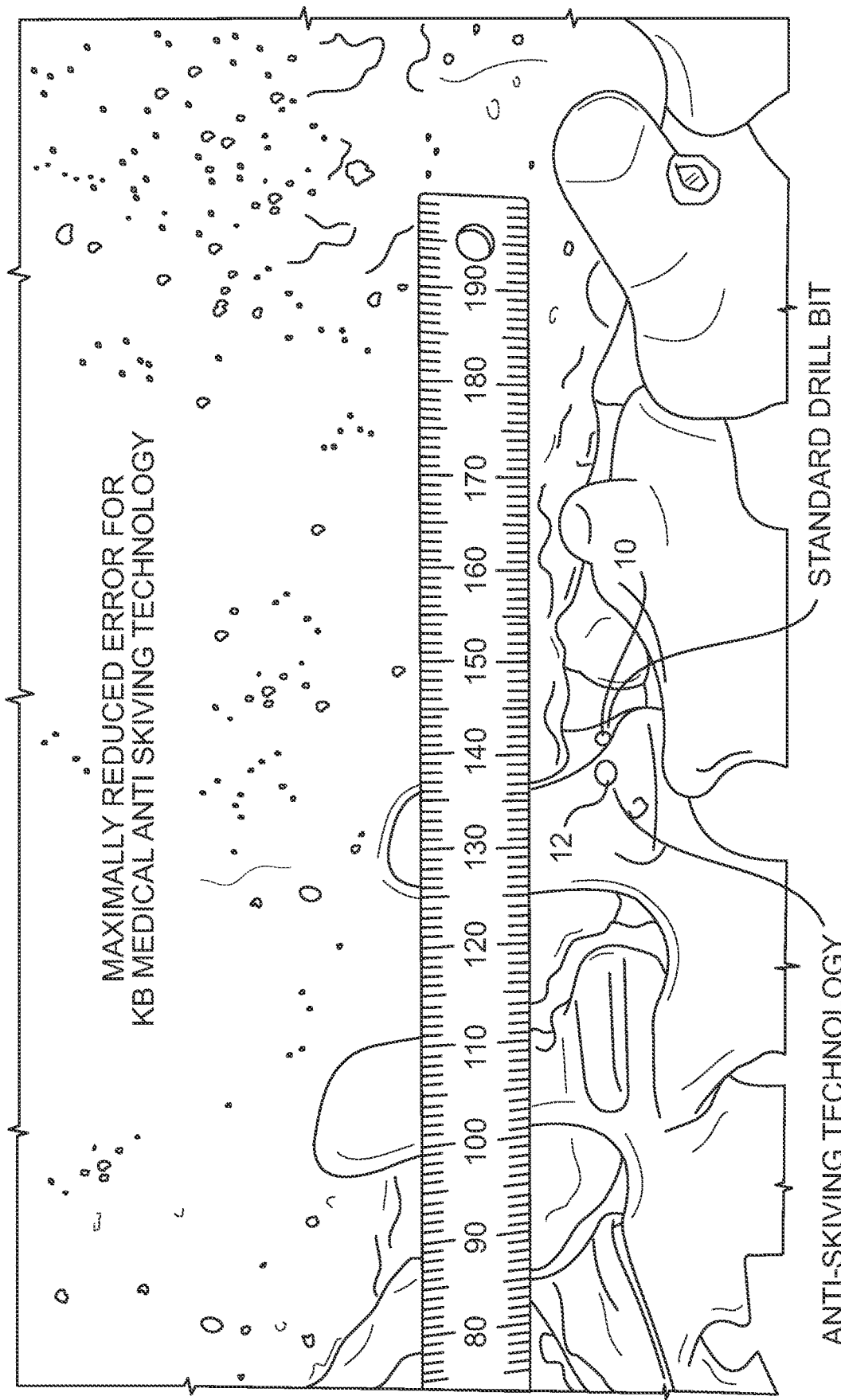
FIG. 1 is an illustration of drilling a hole using anti-skiving technology and drilling a hole without using anti-skiving technology.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF THE DRAWINGS

The present application incorporates by reference in its entirety the contents of U.S. patent application Ser. No. 14/266,769, filed Apr. 30, 2014, entitled "Apparatus and Systems for Precise Guidance of Surgical Tools"; U.S. patent application Ser. No. 14/602,627, filed Jan. 22, 2015, entitled "Sterile Drape and Adapter for Covering a Robotic Surgical Arm and Preventing Contamination of a Sterile Field"; U.S. patent application Ser. No. 14/695,154, filed Apr. 24, 2015, entitled Surgical Instrument Holder for use with a Robotic Surgical System"; U.S. Patent Application No. 62/395,795, filed Sep. 16, 2016, entitled "Anti-Skid Surgical Instrument for use in Preparing Holes in Bone Tissue"; U.S. Patent Application No. 62/278,313, filed Jan. 13, 2016, entitled "Anti-Skid Surgical Instrument for use in Preparing Holes in Bone Tissue"; U.S. patent application Ser. No. 14/799,170, filed Jul. 14, 2015, entitled "Anti-Skid Surgical Instrument for use in Preparing Holes in Bone Tissue."

Among other things, the disclosed technology relates to intra-operative planning of surgeries using robotic surgical systems and haptic control. Examples of such a system are described in U.S. patent application Ser. No. 14/266,769, filed Apr. 30, 2014, entitled "Apparatus and Systems for Precise Guidance of Surgical Tools", the contents of which are hereby incorporated by reference in its entirety.

Furthermore, the disclosed technology includes methods and systems for stabilizing the robotic surgical system on the operation room floor. Additionally, the disclosed technology includes various components utilized in or with the robotic surgical system, such as a sterile drape and an instrument holder. A sterile drape for use with the disclosed technology is described in U.S. patent application Ser. No. 14/602,627, filed Jan. 22, 2015, entitled "Sterile Drape and Adapter for Covering a Robotic Surgical Arm and Preventing Contamination of a Sterile Field", the contents of which are hereby incorporated by reference in its entirety. An example instrument holder that can be used with the disclosed technology is described in U.S. patent application Ser. No. 14/695,154, filed Apr. 24, 2015, entitled Surgical Instrument Holder for use with a Robotic Surgical System", the contents of which are hereby incorporated by reference in its entirety.

The present application relates to robotic surgical systems for assisting surgeons during spinal, neuro, and orthopedic surgery. The disclosed technology provides surgeons with the ability to perform precise, cost-effective robotic-assisted surgery. The disclosed technology may improve patients' outcome and quality of life as well as reduce the radiation received by the operation room team during surgery.

In one exemplary embodiment, a surgical robotic system provides haptic steering and force feedback and integrates with existing standard instruments. In another exemplary embodiment, the surgical system can be integrated with existing surgical methods, including open, minimally invasive, or percutaneous procedures with or without assistance of a navigation system.

FIG. 1 is an illustration of using anti-skiving technology to improve hole placement accuracy. Skiving occurs when drill bit goes off the trajectory due to drilling at an angle different than the right angle to the surface. Skiving is a well-known and documented problem for robots used in surgery, such as spinal surgery. The disclosed technology, including the robot, control system and specially designed drill bit, enables skiving to be practically removed. Examples of this technology are described in U.S. Patent Application No. 62/395,795, filed Sep. 16, 2016, entitled "Anti-Skid Surgical Instrument for use in Preparing Holes in Bone Tissue", U.S. Patent Application No. 62/278,313, filed Jan. 13, 2016, entitled "Anti-Skid Surgical Instrument for use in Preparing Holes in Bone Tissue", and U.S. patent application Ser. No. 14/799,170, filed Jul. 14, 2015, entitled "Anti-Skid Surgical Instrument for use in Preparing Holes in Bone Tissue", the contents of each of which are hereby incorporated by reference in their entirety. Anti-skiving (also referred to as anti-skid) technology can be used in robotic surgery, with difficult patient anatomy, and for revision surgeries.

The present disclosure provides a surgical robot that includes a robotic arm mounted on a mobile cart. An actuator may move the robotic arm. The robotic arm may include a force control end-effector configured to hold a surgical tool. The robot may be configured to control and/or allow positioning and/or movement of the end-effector with at least four degrees of freedom (e.g., six degrees of freedom, three translations and three rotations).

In some implementations, the robotic arm is configured to releasably hold a surgical tool, allowing the surgical tool to be removed and replaced with a second surgical tool. The system may allow the surgical tools to be swapped without re-registration, or with automatic or semi-automatic re-registration of the position of the end-effector.

In some implementations, the surgical system includes a surgical robot, a tracking detector that captures the position of the patient and different components of the surgical robot, and a display screen that displays, for example, real time patient data and/or real time surgical robot trajectories.

In some implementations, a tracking detector monitors the location of patient and the surgical robot. The tracking detector may be a camera, a video camera, an infrared detector, field generator and sensors for electro-magnetic tracking or any other motion detecting apparatus. In some implementation, based on the patient and robot position, the display screen displays a projected trajectory and/or a proposed trajectory for the robotic arm of robot from its current location to a patient operation site. By continuously monitoring the patient and robotic arm positions, using tracking detector, the surgical system can calculate updated trajectories and visually display these trajectories on display screen to inform and guide surgeons and/or technicians in the operating room using the surgical robot. In addition, in certain embodiments, the surgical robot may also change its position and automatically position itself based on trajectories calculated from the real time patient and robotic arm positions captured using the tracking detector. For instance, the trajectory of the end-effector can be automatically adjusted in real time to account for movement of the vertebrae or other part of the patient during the surgical procedure.

Now turning to drawings, FIG. 1 illustrates entry holes created by a standard drill bit and an enhanced drill bit according to one embodiment of the present application. In this exemplary embodiment, an enhanced drill bit is provided which creates an entry hole 12 that is generally larger than non-enhanced drill bill. The enhanced drill bit provides anti-skiving features and produces a larger entry hole to minimizes errors that may occur during surgery causing by skiving.

Figure 2A:
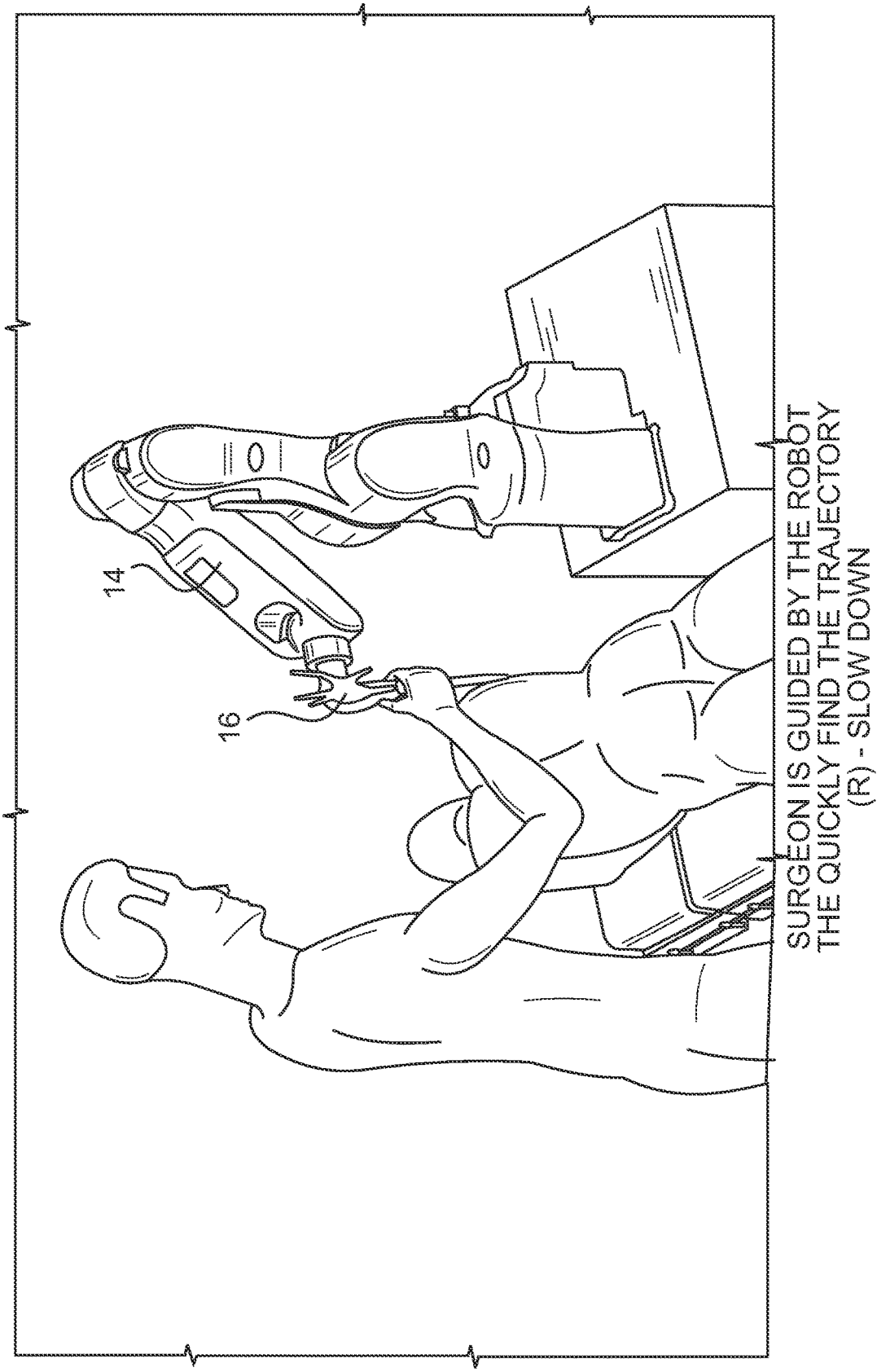
FIGS. 2A-2C illustrate a trajectory snap feature.
Figure 2B:
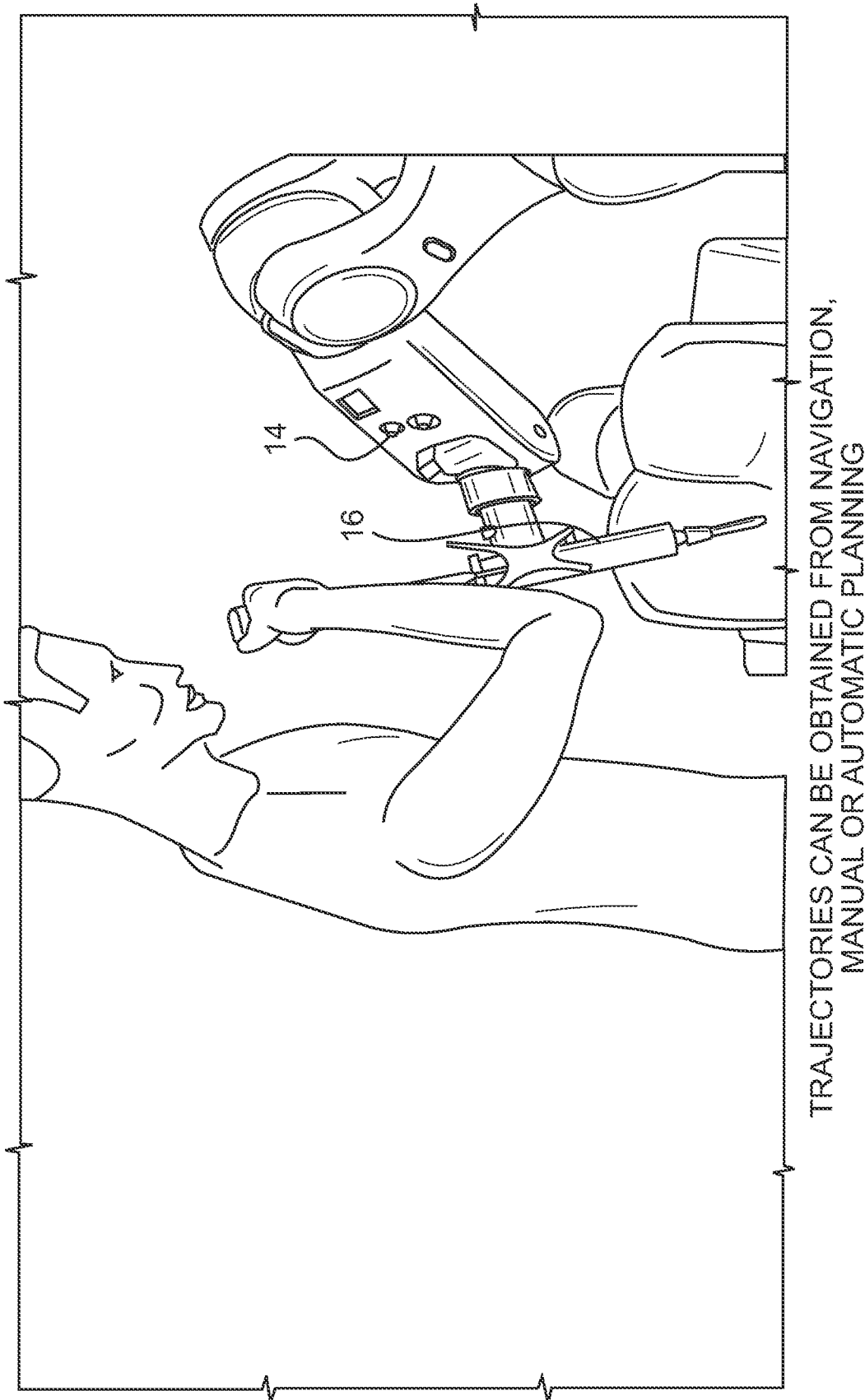
Figure 2C:
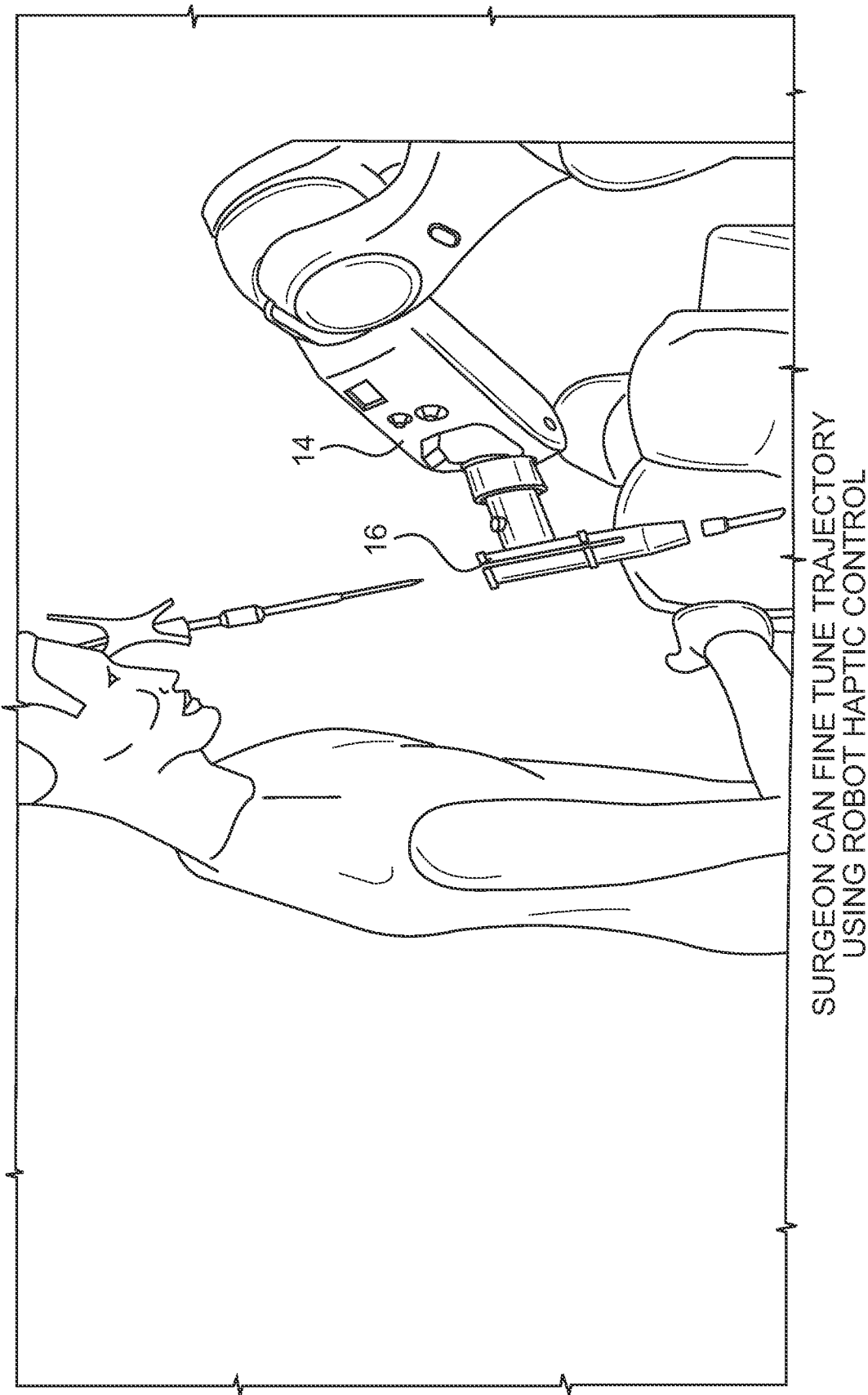

FIGS. 2A-2C illustrate a surgical robotic system that includes a robot arm 14, and an end effector 16 that is positioned over a patient. In one embodiment, there is a trajectory "snap" feature that allows optimal positioning of the end effector 16 on a preferred trajectory. In certain embodiments, a surgeon must move the robotic arm 14 so that the end effector 16 is near the desired trajectory for the operation. Rather than have the surgeon perfectly alight the end-effector with the trajectory, the robot arm 14 can move the end-effector 16 so that it is appropriately positioned relative to the trajectory once the end-effector is within a threshold distance of the trajectory.

In certain embodiments, once the end-effector 16 is within a threshold distance of the desired trajectory, the robotic surgical system may automatically move (e.g., at a pre-programmed pace) the end effector 16 such that the end-effector is appropriately positioned along the trajectory. The threshold distance can be greater than zero (e.g., greater than 0.1 cm, 0.5 cm, or 1 cm) and less than 1 meter (e.g., less than 20 cm, 10 cm, 5 cm, 3 cm).

In manual surgery, the trajectory has to be found four times: before incision, when drilling, when tapping, and when placing screw. Using the disclosed technology, the trajectory is found once and can be maintained or a new trajectory may be used. The disclosed technology, in certain embodiments, assists a user in quickly finding trajectories in space using guiding forces (like gravity or virtual spring). Trajectories can also be planned using navigation techniques and may be downloaded from navigation, planned manually, or planned automatically. The surgeon can at any time fine-tune the trajectory using haptic control. This provides significant potential for time saving in deformity cases.

Figure 3B:
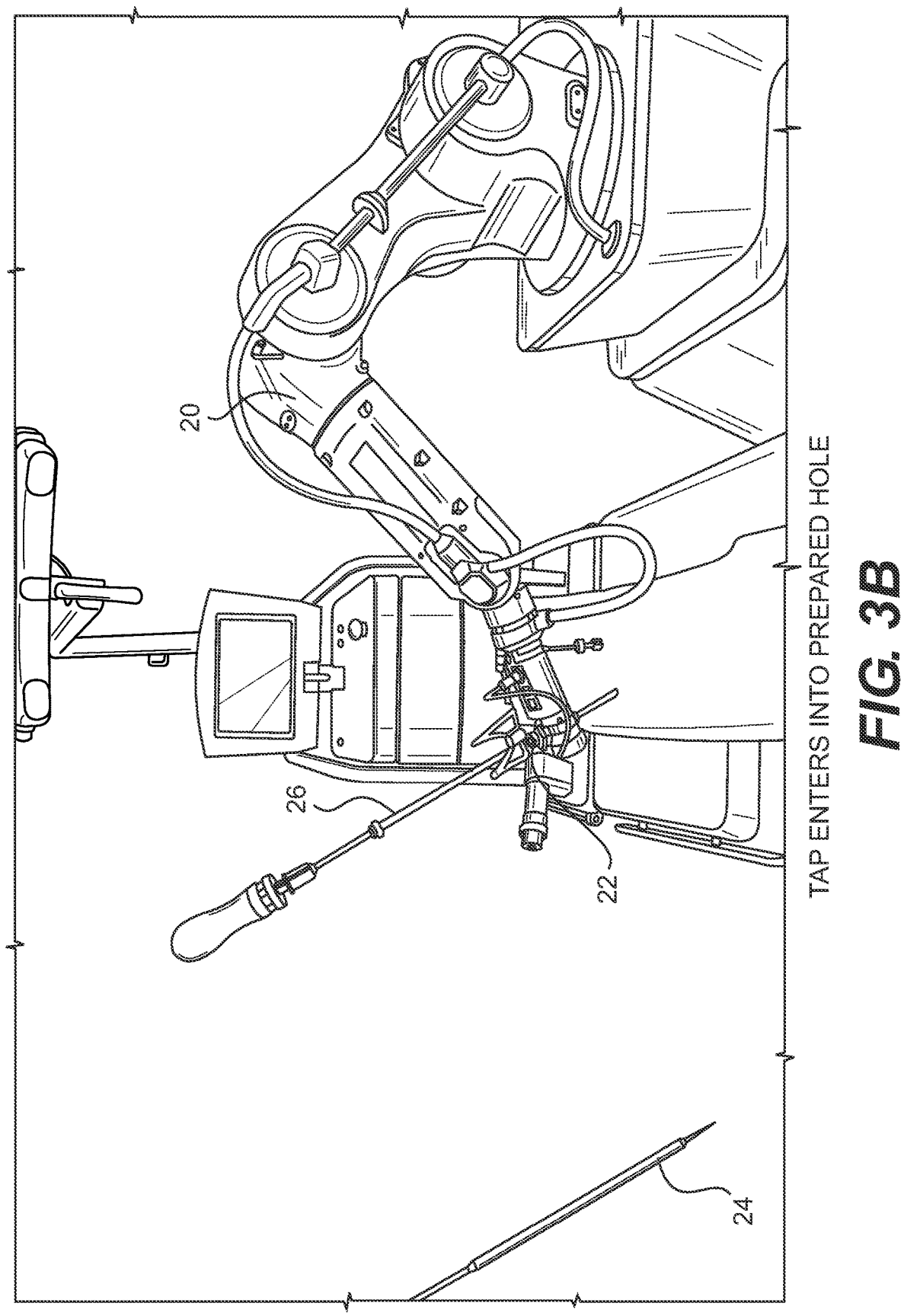

FIGS. 3A-3C illustrates a surgical robotic system that includes a robot arm 20, and a universal instrument guide 22 and associated methods of use. FIG. 3A is an illustration of a drill bit 24 being inserted into the guide 22 held by the robot arm 20 to drill a hole in a bone. Anti-skiving technology as described above can be used for drilling. Next, as shown in FIG. 3B, a tap 26 is used to prepare/create threads in the hole. Finally, as shown in FIG. 3C, an instrument 26 is used to place a screw in the tapped hole. This can be accomplished using the disclosed technology without the need for a k-wire. Accordingly, a user can drill, tap and place a screw through the same access channel.

Figure 4A:
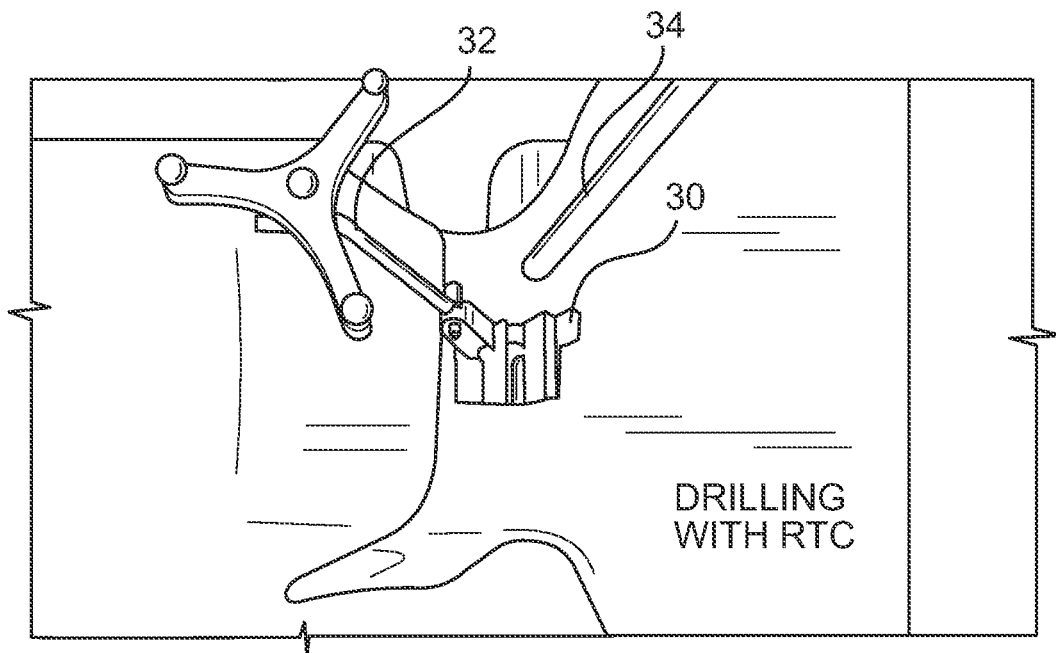
FIGS. 4A and 4B illustrate a hole being drilled in bone using real-time compensation.
Figure 4B:
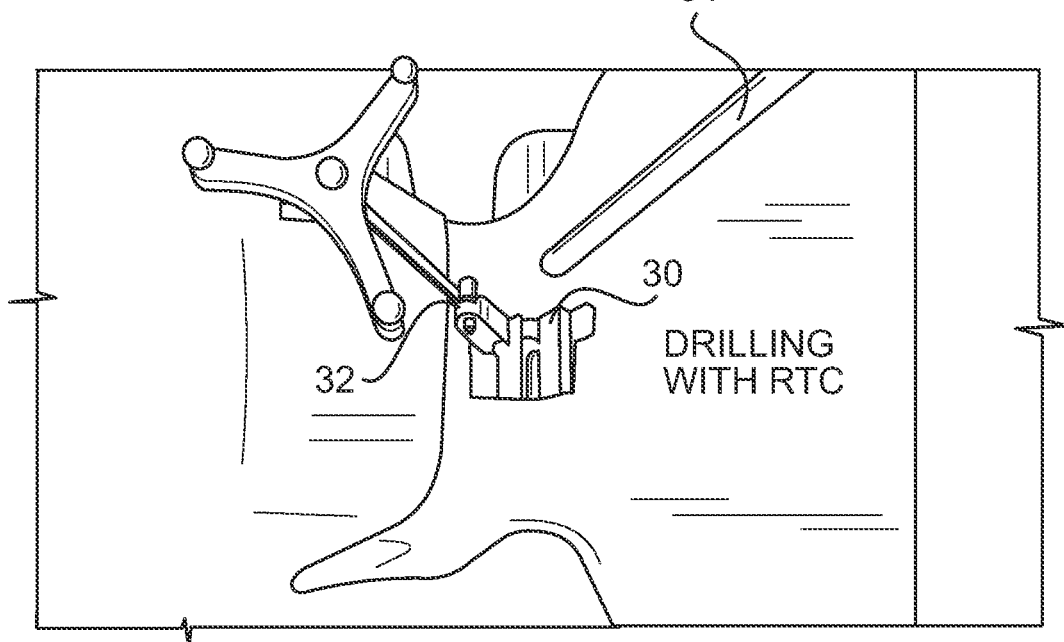

FIGS. 4A and 4B illustrate real-time compensation of the robot arm based on the tracking of optical markers positioned on instruments during the surgical procedure. Specifically, real-time compensation allows the instrument to track the movement of the vertebra. In some situations, the vertebra can move when forces are applied, such as while drilling a hole. In one exemplary embodiment, the robot arm follows the movement of the vertebra in real time using navigation techniques.

In one embodiment, as movement of the vertebra is detected and the robot arm automatically adjusts the position of the instrument based on this detected movement. This feature allows the planned or set trajectory to be maintained.

Specifically, FIG. 4A illustrates the vertebra 30 of a patient and tracking device 32 in a first position and the drill 34 in a first position. As shown in FIG. 4B, the vertebra 30 has moved to a second position and the drill 34 has moved to a corresponding second position automatically based on the tracking of the patient and the instruments. This technique can be used in many surgeries, particularly surgeries that will encounter highly mobile vertebrae, such as cervical and trauma surgeries. In other embodiments, as the vertebra is moved either accidentally or purposefully, the robotic system automatically calculates the movement of the vertebra based on movement and registration of the tracking device 32. Using the monitored movement of the vertebra, the robotic system then automatically causes the robot arm to move to the planned trajectory based on the second position of the vertebra.

Figure 5A:
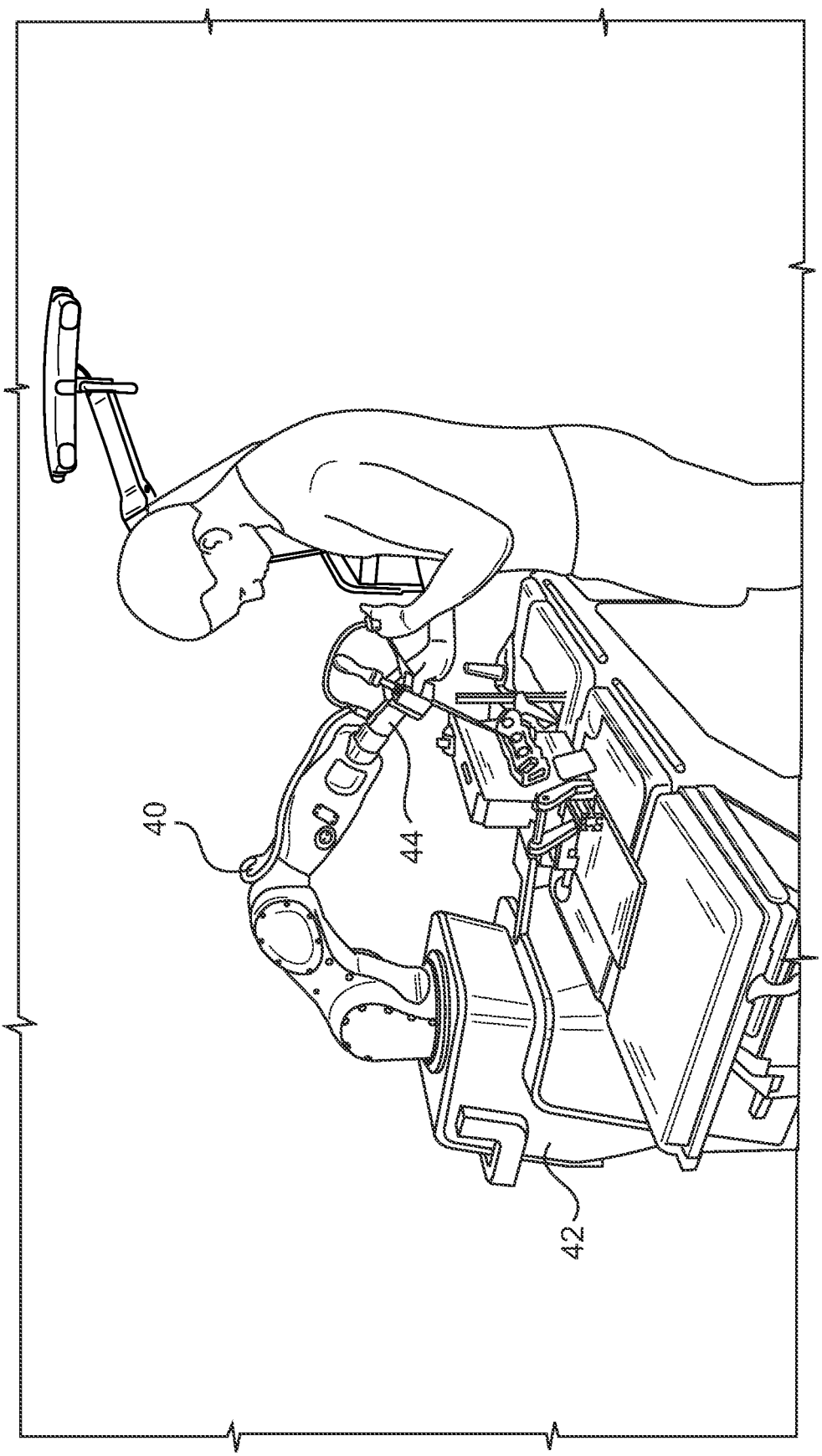
FIGS. 5A-5E illustrate robotic guiding of surgical instruments.
Figure 5B:
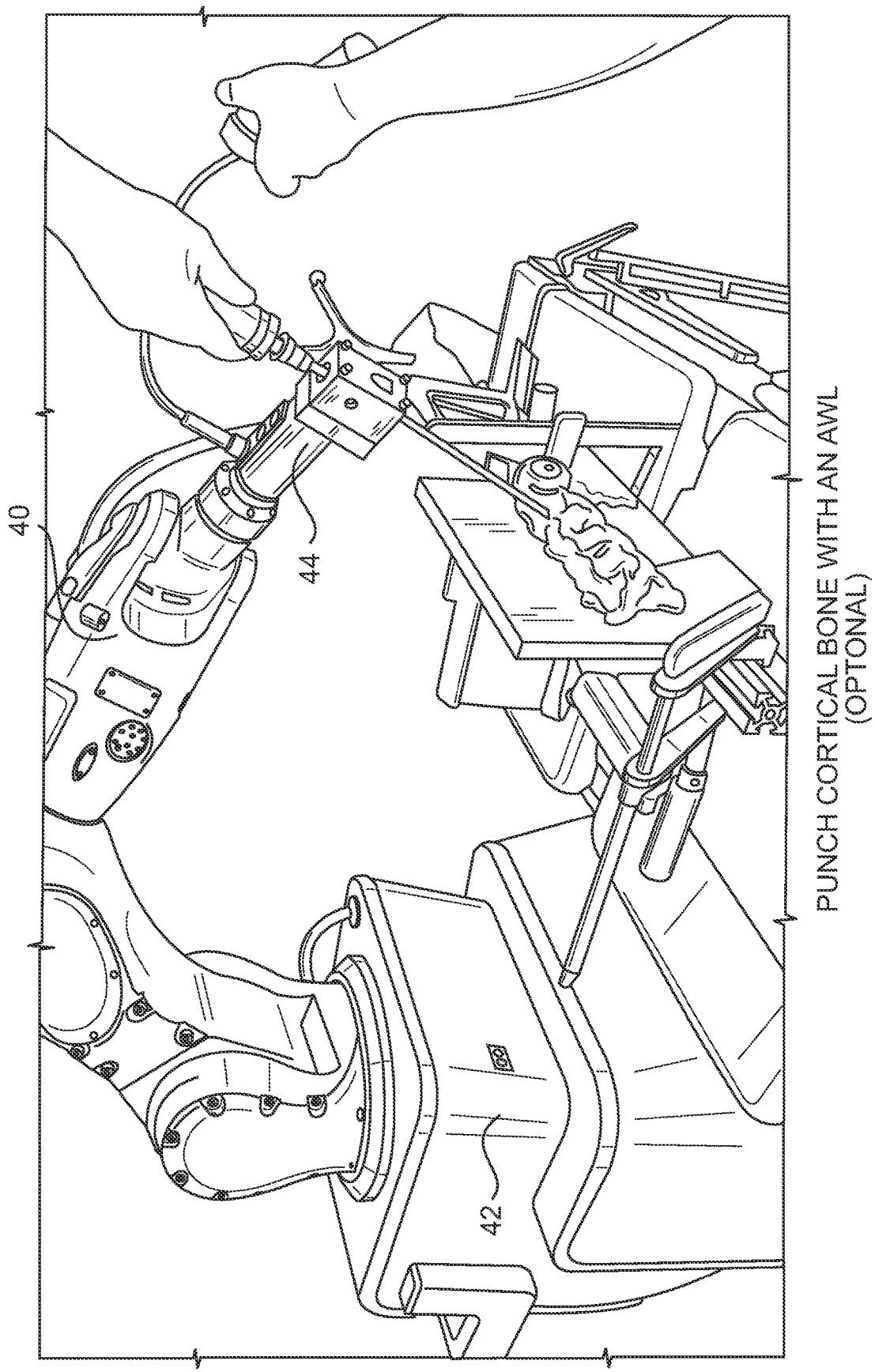
Figure 5C:
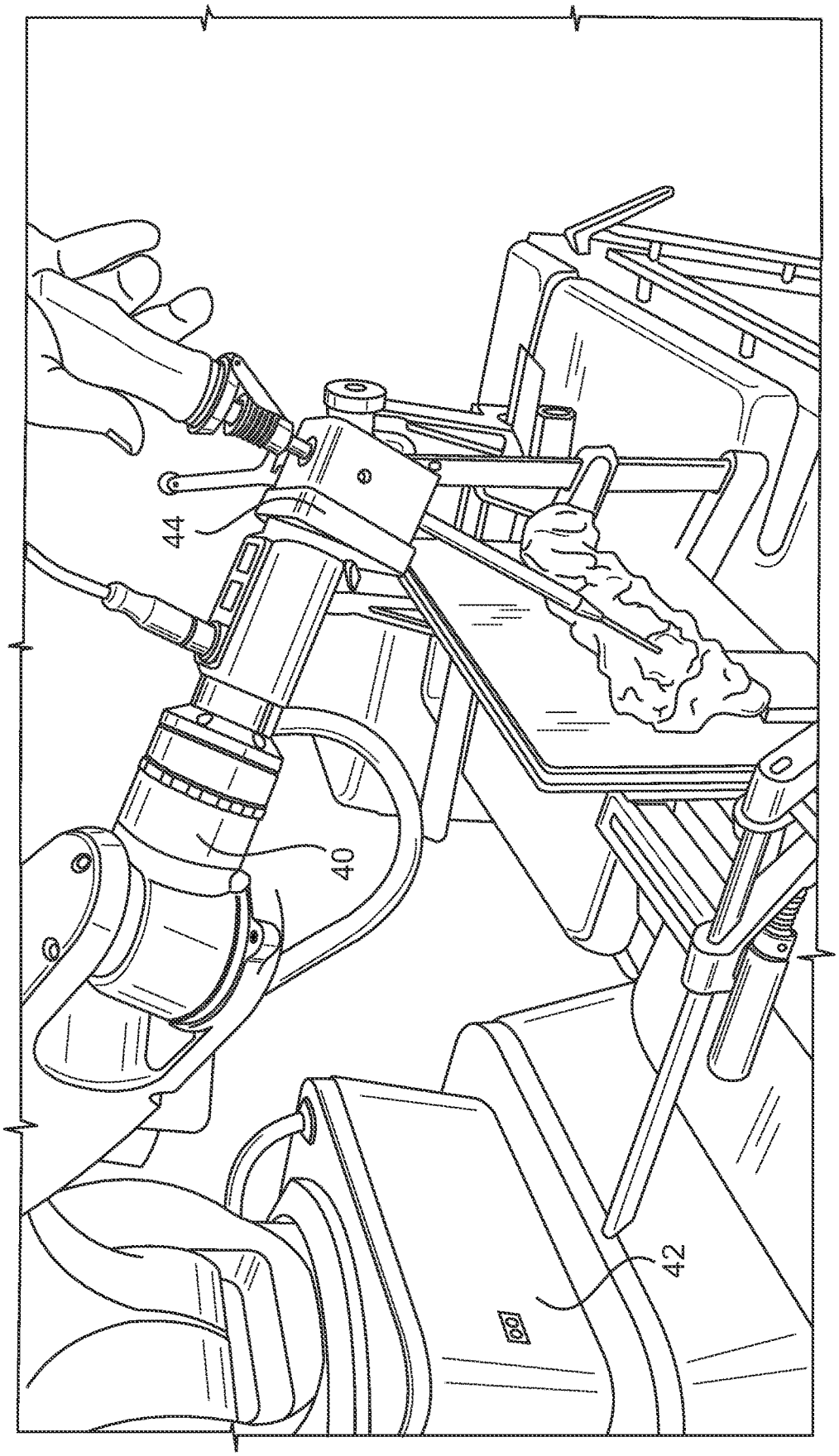
Figure 5D:
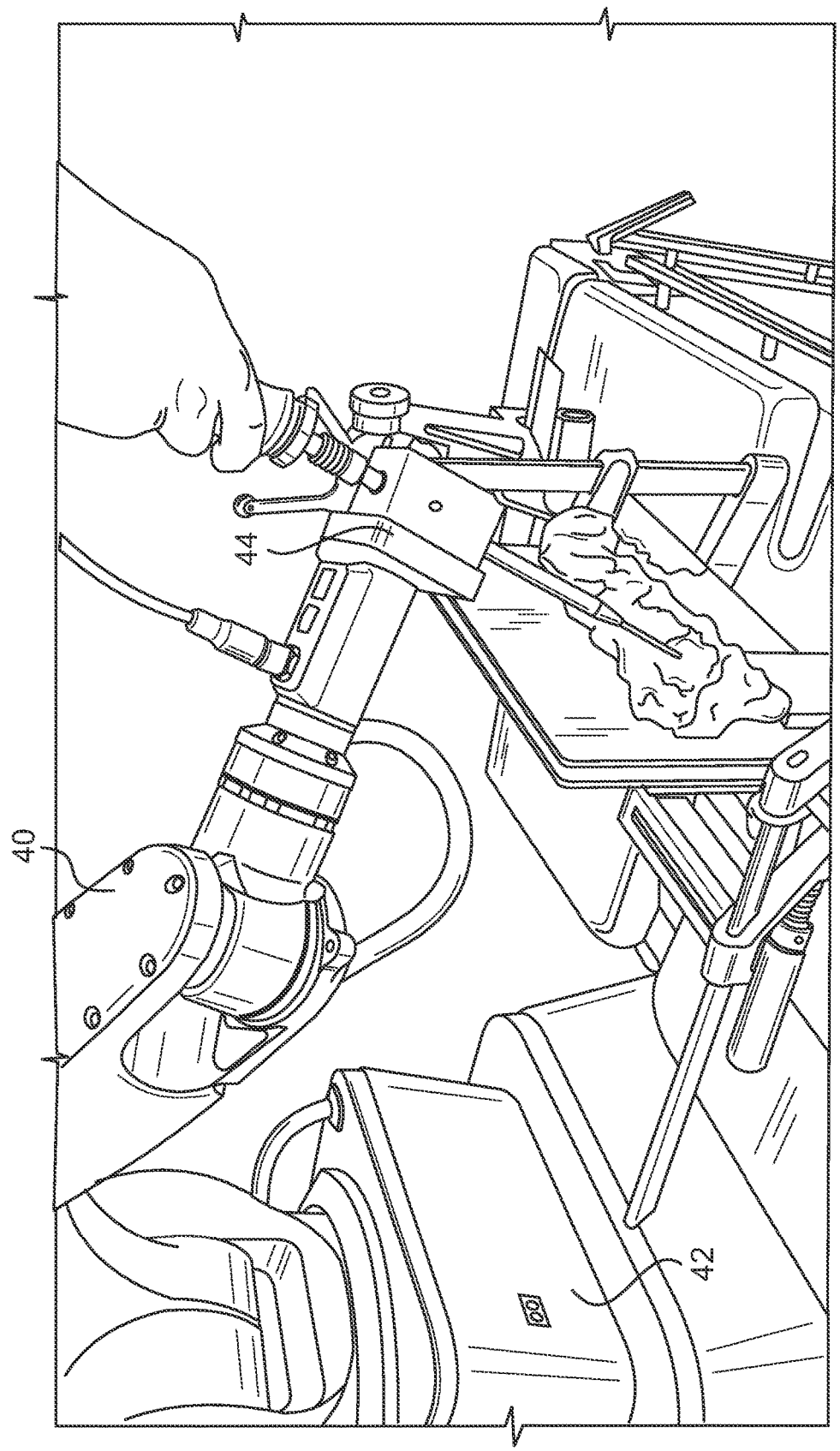
Figure 5E:
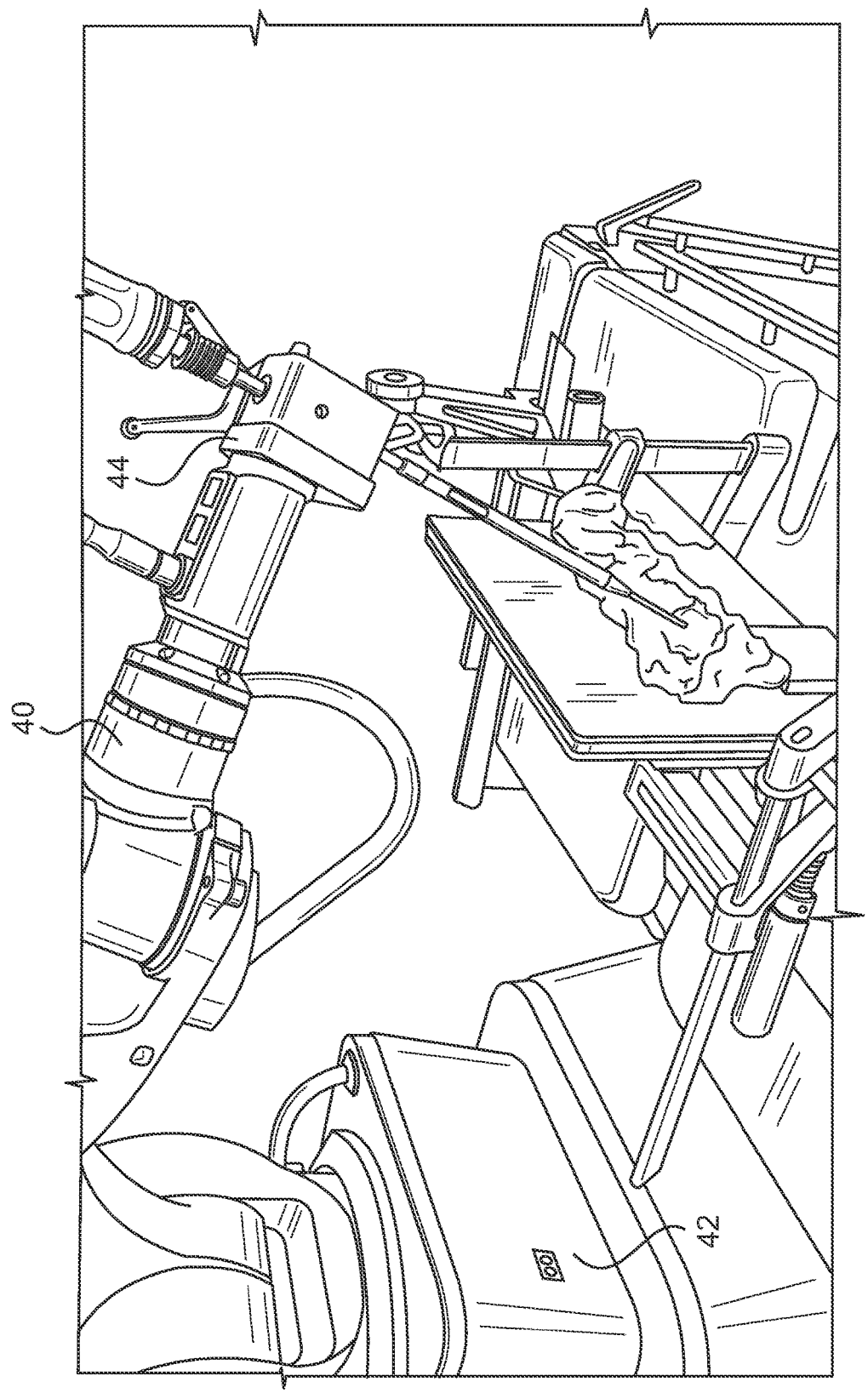

FIG. 5A illustrates a user planning a trajectory. In one embodiment, there is a robotic arm 40 coupled to a base 42. The robotic arm 40 includes an end effector 44 that is configured to receive an instrument 46 for performing surgical procedures. A user can move the robotic arm 40 with the instrument 46 (e.g., pointer) held by the end-effector 44 to a desired trajectory. The user can then select to have the particular trajectory saved by within a computer processor of the robotic surgical system. Alternatively, the trajectory can be obtained through real-time navigation or tracking of the instrument 46 and the patient through the use of optical markers. As shown in FIG. 5B, in certain embodiments, the vertebra can be punched with an instrument 46 such as an awl. As shown in FIG. 5C, the hole is drilled and tapped to prepare for insertion of a screw. In certain embodiments, as shown in FIG. 5D, the robot arm is in trajectory-lock mode and follows the advancement of an instrument 46. This can be accomplished by measuring the force applied to the instrument by the user via a force sensor coupled at the end effector and moving the robotic arm in accordance with this force. The force sensor is configured to sense and measure all forces applied to the end effector. These force sensor is capable of measuring forces in the x, y, and z directions. Next, as shown in FIG. 5E, a screw is placed in the tapped hole. In other embodiments, the instrument 46 may be a drill, a tap, k-wire or anything instrument 46 suited to be used for a particular spinal procedure.

Figure 6:
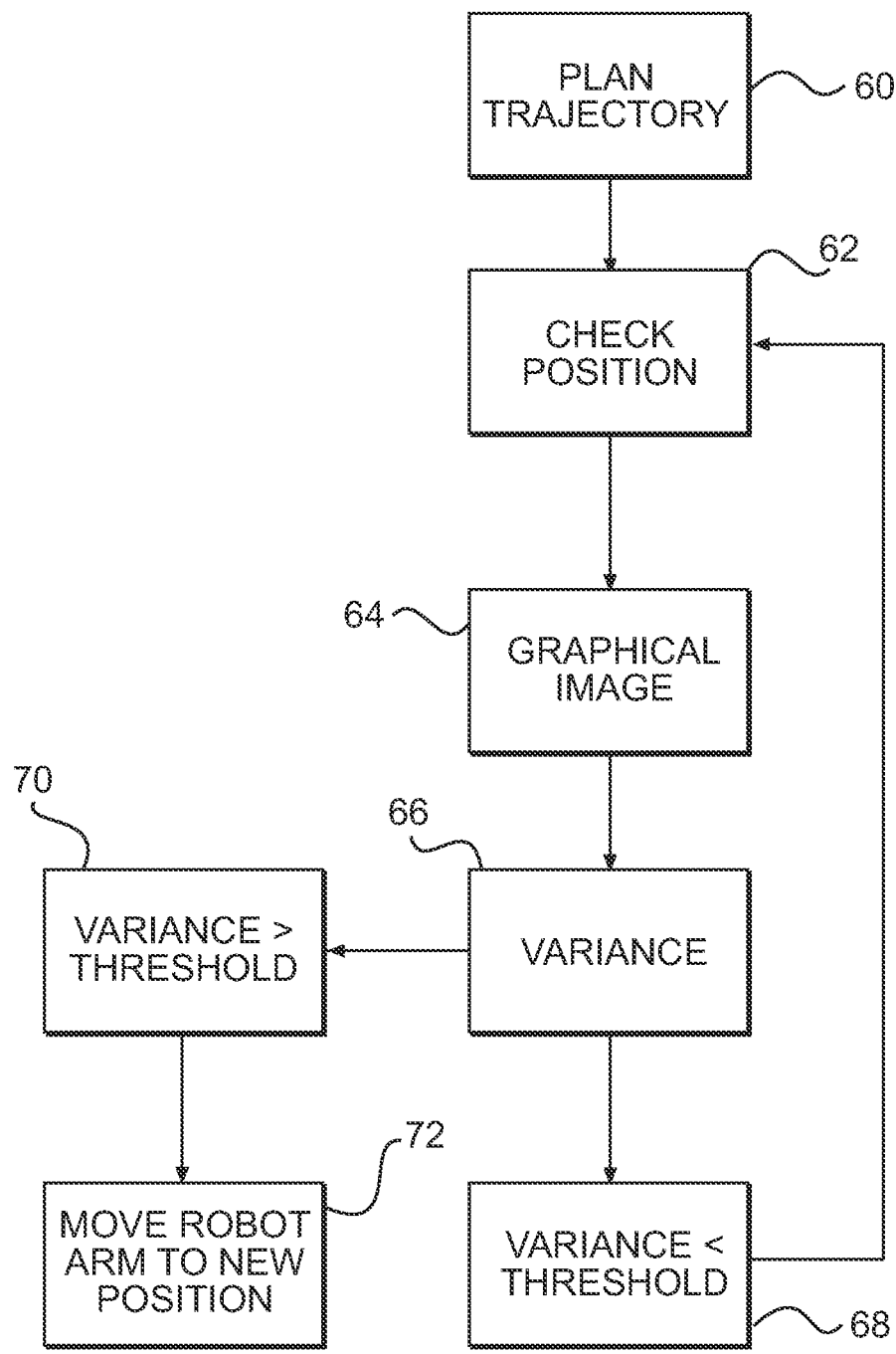
FIG. 6 illustrates a flowchart providing the operational features of the invention according to one exemplary embodiment.

FIG. 6 illustrates a flow chart of the feedback system according to one exemplary embodiment of the present application. A user provides a planned trajectory 60 for positioning the robot arm and end effector through the use of navigation techniques. In one exemplary embodiment the planned trajectory is the directional position of the end effector so that a pedicle screw may be placed in the vertebra. In other embodiments, the planned trajectory may align the end effector so that an intervertebral spacer may be positioned through the end effector in the intervertebral space of adjacent vertebral bodies. In another embodiment, the planned trajectory may align the end effector so that a bone plate may be positioned on adjacent vertebral bodies. In other embodiments, the planned trajectory may be a procedure such a biopsy, a discectomy, bone graft implementation, kyphoplasty, vertebroplasty.

Turning back to FIG. 6, once the planned trajectory is provided to the computer system operating the robotic arm, the system continuously checks the position of the end effector with planned trajectory positions and provides a graphical image 64 of the planned positioning of the end effector and the actual positioning of the end effector. The variance 66 between the planned trajectory and actual positioning of the end effector and the patient is calculated and imaged to the user. If the variance is less than a threshold distance 68, then robot arm remains unmoved from the planned trajectory and the computer system rechecks the position of the end effector 62 in view of the patient. If the variance is greater than a threshold distance 70, the feedback system will signal the actuator of the robot arm to move the end effector to the planned trajectory based on the position of the patient and the instruments that are navigated by the optical system. In some embodiments, if the patient is moved accidentally, the threshold variance will be greater than the planned trajectory variance and the robot arm will move the end effector to the new trajectory that is within the threshold distance. In one exemplary embodiment, the threshold distance may be greater than 0.1 cm, 0.5 cm, or 1 cm or less than 1 meter (less than 20 cm, 10 cm, 5 cm, 3 cm). In certain embodiments, the robotic surgical system continuously checks the threshold distances in real-time. In other embodiments, the user may input a number of reviews of the threshold distances to minimizes robotic arm movements.

In certain embodiments, the disclosed technology is used for volume removal. For example, the disclosed technology can be used for orthopedic surgery, such as unilateral knee replacement. No-go zones, such as locations of nerves and tendons, can be defined before the procedure is performed. Stay-in zones (volume for implant placement—"negative" of the implant) can also be defined. A surgeon can manipulate the robot, directly or remotely, to perform the robot. However, the robot can ensure that the instrument used attached to the end-effector does not enter a no-go zone remains within a stay-in zone. This provides quick and precise implant placement in accordance with planning. Furthermore, the system can be fully interactive such that the surgeon remains in control the entire time.

In certain embodiments, the disclosed technology can be used for rod bending. For example, the system can bend rods for use in deformity cases. The system provides quick, easy and automatic rod bending to create the appropriately shaped rod. The desired shape can take into consideration target sagittal balance and actual pedicle screw placement. The system can also provide a small bending radius even when the rod is formed of the hardest materials. In certain embodiments, the robot is "locked" to particular rods only. The rod bending system provides significant time savings and usability improvements.

In view of the structure, functions and apparatus of the systems and methods described here, in some implementations, a system and method for providing a robotic surgical system are provided. Having described certain implementations of methods and apparatus for supporting an robotic surgical systems, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

What is claimed is:

1. A robotic surgical system for performing surgery, the system comprising:
   a robotic arm;
   an end-effector coupled to the robotic arm and configured to hold a first surgical tool;
   an actuator for controlling movement of the robotic arm and positioning of the end-effector;
   optical tracking markers attached to both (i) the end-effector and (ii) a patient;
   an optical tracking detector configured to track the position of the optical tracking markers attached to both the end effector and the patient; and
   a processor and a non-transitory computer readable medium storing instructions thereon wherein the instructions, when executed, cause the processor to:
   access or generate a virtual representation of the patient;
   continuously obtain a real-time (i) end-effector position and (ii) patient position from the optical tracking detector while a surgeon is manually moving the end-effector;
   determine whether the manually moving end-effector is within a first threshold distance of a planned positioning and if within the first threshold distance, automatically move the robotic arm to align the end-effector with the planned positioning;
   after the end-effector has initially aligned with the planned positioning, continuously calculate a variance between the planned positioning and actual positioning of the end-effector;
   continuously provide on a display device a graphic image of the planned positioning and the actual positioning of the end-effector;
   control the actuator to move the end-effector to the planned positioning based only on the actual positions of the patient and the first surgical tool if the calculated variance is greater than a second threshold distance.

2. The system of claim 1, wherein the instructions, when executed, cause the processor to: determine whether the first surgical tool is within the threshold distance of a pre-planned trajectory; and move the robotic arm such that the first surgical tool is appropriately aligned with the trajectory.

3. The system of claim 2, wherein the first threshold distance and the second threshold distance are each greater than zero and less than 20 cm.

4. The system of claim 2, wherein the first threshold distance and the second threshold distance are each greater than 0.1 cm and less than 20 cm.

5. The system of claim 2, wherein the first threshold distance and the second threshold distance are each greater than 1 cm and less than 3 cm.

6. The system of claim 2, wherein the first threshold distance and the second threshold distance are each greater than 0.5 cm and less than 5 cm.

7. The system of claim 1, wherein the end effector is configured to receive a second surgical tool for performing surgical procedures.

8. The system of claim 1, wherein the first surgical tool is a drill bit.

9. The system of claim 1, wherein the first surgical tool is an awl.

10. The system of claim 1, wherein the first surgical tool is used to position a pedicle screw in bone.

11. The system of claim 1, wherein the first surgical tool includes optical markers for tracking by the optical tracking detector.

12. A robotic surgical system for performing surgery, the system comprising:
   a robotic arm;
   an end-effector attached to the robotic arm and configured to hold a first surgical tool, the end-effector having an optical tracking marker, wherein the robot arm is automatically moved to a planned positioning when the end-effector being initially manually moved by a surgeon is determined to be within a first threshold distance from the planned positioning;
   an optical tracking marker array configured to be attached to a patient;
   an actuator for controlling movement of the robotic arm and the end-effector;
   an optical tracking detector for real time detection of (i) the end-effector position and (ii) patient position by detection of the optical marker attached to the end-effector and optical marker array attached to the patient; and
   a feedback system for calculating a variance between the planned positioning and actual positioning of the end-effector based on output from the optical tracking detector, and for controlling the actuator to move the end-effector to the planned positioning based only on the actual positions of the patient and the first surgical tool if the calculated variance is greater than a second threshold distance.

13. The system of claim 12, wherein the feedback system, includes a force sensor that calculates the movement of the end effector away from the planned positioning the threshold distance and moves the robotic arm such that the first surgical tool is aligned with a planned trajectory.

14. The system of claim 12, wherein the first threshold distance and the second threshold distance are each greater than zero and less than 20 cm.

15. The system of claim 12, wherein the first threshold distance and the second threshold distance are each greater than 0.1 cm and less than 20 cm.

16. The system of claim 12, wherein the first threshold distance and the second threshold distance are each greater than 1 cm and less than 3 cm.

17. The system of claim 12, wherein the first threshold distance and the second threshold distance are each greater than 0.5 cm and less than 5 cm.

* * * * *